(12) United States Patent
Moen

(10) Patent No.: US 9,920,368 B2
(45) Date of Patent: Mar. 20, 2018

(54) METHODS FOR DETECTING DNA POLYMORPHISMS IN ATLANTIC SALMON

(71) Applicant: Aqua Gen AS, Trondheim (NO)

(72) Inventor: Thomas Moen, Aas (NO)

(73) Assignee: Aqua Gen AS, Trondheim (NO)

( * ) Notice: Subject to any disclaimer, the term of this patent is extended or adjusted under 35 U.S.C. 154(b) by 0 days.

(21) Appl. No.: 14/412,829

(22) PCT Filed: Jul. 8, 2013

(86) PCT No.: PCT/GB2013/051800
§ 371 (c)(1),
(2) Date: Jan. 5, 2015

(87) PCT Pub. No.: WO2014/006428
PCT Pub. Date: Jan. 9, 2014

(65) Prior Publication Data
US 2015/0329903 A1  Nov. 19, 2015

(30) Foreign Application Priority Data
Jul. 6, 2012 (GB) .................... 1212069.7

(51) Int. Cl.
*C12Q 1/68* (2006.01)
(52) U.S. Cl.
CPC ......... *C12Q 1/6874* (2013.01); *C12Q 1/6827* (2013.01); *C12Q 1/6888* (2013.01); *C12Q 2600/124* (2013.01)

(58) Field of Classification Search
None
See application file for complete search history.

(56) References Cited

PUBLICATIONS

Hirschhorn et al. Genetics in Medicine. vol. 4, No. 2, pp. 45-61, Mar. 2002.*
Lucentini et al the Scientist (2004) vol. 18, p. 20.*
Hattersley et al. The Lancet. 2005. 366: 1315-1323.*
Storset et al. Aquaculture. 2007. 272S1: S62-S68.*
GenBank Accession No. ET409754.1 NCBI Database (National Center for Biotechnology Information, National Library of Medicine, Bethesda, MD, USA), Mar. 5, 2008.*
Houston RD, Haley CS, Hamilton A, Guy DR, Tinch AE, Taggart JB, McAndrew BJ, Bishop SC (2008) Major quantitative trait loci affect resistance to infectious pancreatic necrosis in Atlantic salmon (*Salmo salar*). Genetics 178: 1109-15.
Houston RD, Davey JW, Bishop SC, Lowe, NR, Mota-Velasco JC et al. (2012) Characterisation of QTL-linked and genome-wide restriction site-associated DNA (RAD) markers in farmed Atlantic salmon. BMC Genomics 13: 244.
Lien S, Gidskehaug L, Moen T, Hayes BJ, Berg PR, Davidson WS, Omholt SW, Kent MP (2011) A dense SNP-based linkage map for Atlantic salmon (*Salmo salar*) reveals extended chromosome homeologies and striking differences in sex-specific recombination patterns. BMC Genomics 12: 615.
Madsen and Jensen (2008) DMU: a user's guide. A package for analysing multivariate mixed models, version 6, release 5.0. University of Aarhus, Tjele, Denmark.
Moen T, Hayes B, Baranski M, Berg PR, Kjøglum S, Koop BF, Davidson WS, Omholt SW, Lien S (2008) A linkage map of the Atlantic salmon (*Salmo salar*) based on EST-derived SNP markers. BMC Genomics 9: 223.
Moen T, Baranski M, Sonesson AK, Kjøglum S (2009) Confirmation and fine-mapping of a major QTL for resistance to infectious pancreatic necrosis in Atlantic salmon (*Salmo salar*): population-level associations between markers and trait. BMC Genomics 10: 368.
Shifman S, Kuypers J, Kokoris M, Yakir B, Darvasi A (2003) Linkage diseuilibrium patterns of the human genome across populations. Human Molecular Genetics 12: 771-776.
Thorsen J, Zhu B, Frengen E, Osoegawa K, de Jong, PJ, Koop BF, Davidson WS, Høyheim B (2005) A highly redundant BAC library of Atlantic salmon (*Salmo salar*): an important tool for salmon projects. BMC Genomics 6: 50.
International Search Report and Written Opinion dated Oct. 4, 2013 for PCT/GB2013/051800.
Gheyas, A. A., et al. "Segregation of infectious pancreatic necrosis resistance QTL in the early life cycle of Atlantic Salmon (*Salmo salar*)." Animal genetics (2010), vol. 41, No. 5: 531-536.
Moen, Thomas. "Breeding for resistance to viral diseases in salmonids." Breeding for disease resistance in farm animals. CABI (2010): 166-179.
Madsen ad Jensen (2008) DMU: a user's guide. A package for analysing multivariate mixed models, version 6, release 5.2. University of Aarhus, Tjele, Denmark.

* cited by examiner

*Primary Examiner* — Carla J Myers
(74) *Attorney, Agent, or Firm* — Abel Law Group, LLP

(57) ABSTRACT

The Invention relates to a method of predicting resistance to infectious pancreatic necrosis in salmon, the method comprising determining the alleles present at a DNA polymorphism in the salmon and predicting whether or not the salmon is resistant to infectious pancreatic necrosis based on the determination of the alleles. The invention also relates to a method of selecting a salmon for use as broodstock, wherein the salmon is selected based on the prediction by the first method that the salmon will have resistance to infectious pancreatic necrosis.

6 Claims, 3 Drawing Sheets

SEQUENCE LISTING

```
<160> NUMBER OF SEQ ID NOS: 72

<210> SEQ ID NO 1
<211> LENGTH: 30
<212> TYPE: DNA
<213> ORGANISM: Salmo salar
<220> FEATURE:
<221> NAME/KEY: allele
<222> LOCATION: (1)..(30)
<223> OTHER INFORMATION: Polymorphism 1 resistance allele

<400> SEQUENCE: 1
aagttctttt tttttatat gactatcctt                                    30

<210> SEQ ID NO 2
<211> LENGTH: 30
<212> TYPE: DNA
<213> ORGANISM: Salmo salar
<220> FEATURE:
<221> NAME/KEY: allele
<222> LOCATION: (1)..(30)
<223> OTHER INFORMATION: Polymorphism 2 resistance allele

<400> SEQUENCE: 2
ttgagcacgt gttttgacgg tgtaggaagt                                   30

<210> SEQ ID NO 3
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 3 resistance allele

<400> SEQUENCE: 3
acgtacgcag gcgcacccct gcgatttagt g                                 31

<210> SEQ ID NO 4
<211> LENGTH: 31
<212> TYPE: DNA
<213> ORGANISM: Salmo salar
<220> FEATURE:
```

```
<221> NAME/KEY: allele
<222> LOCATION: (1)..(31)
<223> OTHER INFORMATION: Polymorphism 4 resistance allele

<400> SEQUENCE: 4
gggaggtcag tggggtagac aacttaaagc a                              31

<210> SEQ ID NO 5
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 5 resistance allele

<400> SEQUENCE: 5
tcttcaggaa aaaaaaatat aattagtgat t                              31

<210> SEQ ID NO 6
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 6 resistance allele

<400> SEQUENCE: 6
ctacaaactt tctcatggta tagcaaaaaa t                              31

<210> SEQ ID NO 7
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 7 resistance allele

<400> SEQUENCE: 7
gaatgaaagc acttttttgg tatcctatgc t                              31

<210> SEQ ID NO 8
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 8 resistance allele

<400> SEQUENCE: 8
gtcctaacat tgagctgtgt ttgtttggca g                              31

<210> SEQ ID NO 9
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 9 resistance allele

<400> SEQUENCE: 9
actattttat ctggctcttt caatcagtcc t                              31
```

```
<210> SEQ ID NO 10
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 10 resistance allele

<400> SEQUENCE: 10
gatgatggcc cctagagagt tactgtaatg a                               31

<210> SEQ ID NO 11
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 11 resistance allele

<400> SEQUENCE: 11
acattataaa aacagtatga agtgtacgtg t                               31

<210> SEQ ID NO 12
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 12 resistance allele

<400> SEQUENCE: 12
cagacagaca cctacaagta ggctatgtgt t                               31

<210> SEQ ID NO 13
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 13 resistance allele

<400> SEQUENCE: 13
acaaagtaag gtgggtggtg cagagttagg c                               31

<210> SEQ ID NO 14
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 14 resistance allele

<400> SEQUENCE: 14
agtttcaaat gaaatgtgaa tccttcagga t                               31

<210> SEQ ID NO 15
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 15 resistance allele
```

-continued

<400> SEQUENCE: 15
ggtgaaatca tcgtgtatag gctatcacag t                              31

<210> SEQ ID NO 16
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 16 resistance allele

<400> SEQUENCE: 16
gagtacagtg cactccgaca gacaggcaca c                              31

<210> SEQ ID NO 17
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 17 resistance allele

<400> SEQUENCE: 17
tttttgagga ggagggaaat acattgtgtt c                              31

<210> SEQ ID NO 18
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 18 resistance allele

<400> SEQUENCE: 18
tctttcacac atgactccgt aatcccgtta c                              31

<210> SEQ ID NO 19
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 19 resistance allele

<400> SEQUENCE: 19
gcaggcagcg cttgatggcg aattgttttg a                              31

<210> SEQ ID NO 20
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 20 resistance allele

<400> SEQUENCE: 20
cattttatgc attatgtatc agtgatgtta c                              31

<210> SEQ ID NO 21
<211> LENGTH: 31
<212> TYPE: DNA
<213> ORGANISM: Salmo salar

```
<220> FEATURE:
<221> NAME/KEY: allele
<222> LOCATION: (1)..(31)
<223> OTHER INFORMATION: Polymorphism 21 resistance allele

<400> SEQUENCE: 21
agacataggc tcaaataatt cctcactgag g                              31

<210> SEQ ID NO 22
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 22 resistance allele

<400> SEQUENCE: 22
agtgtgttgc acatcctgtc atgcagacaa t                              31

<210> SEQ ID NO 23
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 23 resistance allele

<400> SEQUENCE: 23
cacactttgt caacaaacac atattatgtt a                              31

<210> SEQ ID NO 24
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 24 resistance allele

<400> SEQUENCE: 24
ctgctaatgt cctttggtgg gtttcttttg g                              31

<210> SEQ ID NO 25
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 25 resistance allele

<400> SEQUENCE: 25
gtaacgggat tacggagtca tgtgtgaaag a                              31

<210> SEQ ID NO 26
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 26 resistance allele

<400> SEQUENCE: 26
tcaaaacaat tcgccatcaa gcgctgcctg c                              31
```

<210> SEQ ID NO 27
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 27 resistance allele

<400> SEQUENCE: 27
actcccagtg ctaagtgaag tctccaacat t                                31

<210> SEQ ID NO 28
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 28 resistance allele

<400> SEQUENCE: 28
cctcctctcc ctcccggagt ctgatgcaat t                                31

<210> SEQ ID NO 29
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 29 resistance allele

<400> SEQUENCE: 29
attcattaat ccagcaatag ttactggcac c                                31

<210> SEQ ID NO 30
<211> LENGTH: 31
<212> TYPE: DNA
<213> ORGANISM: Salmo salar
<220> FEATURE:
<221> NAME/KEY: misc_feature
<222> LOCATION: (1)..(31)
<223> OTHER INFORMATION: Polymorphism 30 resistance allele

<400> SEQUENCE: 30
tgccagagac ccccagtgga gcgttcaggg t                                31

<210> SEQ ID NO 31
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 31 resistance allele

<400> SEQUENCE: 31
agtcaaccgc agtactgaag caagactgta g                                31

<210> SEQ ID NO 32
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 32 resistance allele

<400> SEQUENCE: 32
cggaccagga gacagcgacc catcatttca t                                  31

<210> SEQ ID NO 33
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 33 resistance allele

<400> SEQUENCE: 33
gcaatgttca tcctgcttaa ttcaccaaat g                                  31

<210> SEQ ID NO 34
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 34 resistance allele

<400> SEQUENCE: 34
cgctacagaa atgaccgaaa atacacactt c                                  31

<210> SEQ ID NO 35
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 35 resistance allele

<400> SEQUENCE: 35
agatttagga gggtttgctc aaaataagaa a                                  31

<210> SEQ ID NO 36
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 36 resistance allele

<400> SEQUENCE: 36
ttattcggtg gtacctactc tcagaaatct t                                  31

<210> SEQ ID NO 37
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 1 non-resistance allele

<400> SEQUENCE: 37
aagttctttt ttttatata tgactatcct t                                   31

<210> SEQ ID NO 38
<211> LENGTH: 32
<212> TYPE: DNA

```
<213> ORGANISM: Salmo salar
<220> FEATURE:
<221> NAME/KEY: allele
<222> LOCATION: (1)..(32)
<223> OTHER INFORMATION: Polymorphism 2 non-resistance allele

<400> SEQUENCE: 38
ttgagcacgt gttttatgac ggtgtaggaa gt                              32

<210> SEQ ID NO 39
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 3 non-resistance allele

<400> SEQUENCE: 39
acgtacgcag gcgcatccct gcgatttagt g                               31

<210> SEQ ID NO 40
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 4 non-resistance allele

<400> SEQUENCE: 40
gggaggtcag tggggcagac aacttaaagc a                               31

<210> SEQ ID NO 41
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 5 non-resistance allele

<400> SEQUENCE: 41
tcttcaggaa aaaatatat aattagtgat t                                31

<210> SEQ ID NO 42
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 6 non-resistance allele

<400> SEQUENCE: 42
ctacaaactt tctcaaggta tagcaaaaaa t                               31

<210> SEQ ID NO 43
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 7 non-resistance allele

<400> SEQUENCE: 43
gaatgaaagc actttcttgg tatcctatgc t                               31
```

<210> SEQ ID NO 44
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 8 non-resistance allele

<400> SEQUENCE: 44
gtcctaacat tgagccgtgt ttgtttggca g                              31

<210> SEQ ID NO 45
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 9 non-resistance allele

<400> SEQUENCE: 45
actattttat ctggcccttt caatcagtcc t                              31

<210> SEQ ID NO 46
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 10 non-resistance allele

<400> SEQUENCE: 46
gatgatggcc cctagtgagt tactgtaatg a                              31

<210> SEQ ID NO 47
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 11 non-resistance allele

<400> SEQUENCE: 47
acattataaa aacagcatga agtgtacgtg t                              31

<210> SEQ ID NO 48
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 12 non-resistance allele

<400> SEQUENCE: 48
cagacagaca cctaccagta ggctatgtgt t                              31

<210> SEQ ID NO 49
<211> LENGTH: 31
<212> TYPE: DNA
<213> ORGANISM: Salmo salar
<220> FEATURE:
<221> NAME/KEY: allele
<222> LOCATION: (1)..(31)

-continued

```
<223> OTHER INFORMATION: Polymorphism 13 non-resistance allele

<400> SEQUENCE: 49
acaaagtaag gtgggcggtg cagagttagg c                                   31

<210> SEQ ID NO 50
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 14 non-resistance allele

<400> SEQUENCE: 50
agtttcaaat gaaatatgaa tccttcagga t                                   31

<210> SEQ ID NO 51
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 15 non-resistance allele

<400> SEQUENCE: 51
ggtgaaatca tcgtgcatag gctatcacag t                                   31

<210> SEQ ID NO 52
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 16 non-resistance allele

<400> SEQUENCE: 52
gagtacagtg cactcagaca gacaggcaca c                                   31

<210> SEQ ID NO 53
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 17 non-resistance allele

<400> SEQUENCE: 53
tttttgagga ggaggaaaat acattgtgtt c                                   31

<210> SEQ ID NO 54
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 18 non-resistance allele

<400> SEQUENCE: 54
tctttcacac atgacgccgt aatcccgtta c                                   31

<210> SEQ ID NO 55
<211> LENGTH: 31
```

```
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 19 non-resistance allele

<400> SEQUENCE: 55
gcaggcagcg cttgacggcg aattgttttg a                               31

<210> SEQ ID NO 56
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 20 non-resistance allele

<400> SEQUENCE: 56
cattttatgc attatatatc agtgatgtta c                               31

<210> SEQ ID NO 57
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 21 non-resistance allele

<400> SEQUENCE: 57
agacataggc tcaaagaatt cctcactgag g                               31

<210> SEQ ID NO 58
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 22 non-resistance allele

<400> SEQUENCE: 58
agtgtgttgc acatcgtgtc atgcagacaa t                               31

<210> SEQ ID NO 59
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 23 non-resistance allele

<400> SEQUENCE: 59
cacactttgt caacacacac atattatgtt a                               31

<210> SEQ ID NO 60
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 24 non-resistance allele

<400> SEQUENCE: 60
```
ctgctaatgt cctttgtgg gtttcttttg g   31

<210> SEQ ID NO 61
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 25 non-resistance allele

<400> SEQUENCE: 61
gtaacgggat tacggcgtca tgtgtgaaag a   31

<210> SEQ ID NO 62
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 26 non-resistance allele

<400> SEQUENCE: 62
tcaaaacaat tcgccgtcaa gcgctgcctg c   31

<210> SEQ ID NO 63
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 27 non-resistance allele

<400> SEQUENCE: 63
actcccagtg ctaagggaag tctccaacat t   31

<210> SEQ ID NO 64
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 28 non-resistance allele

<400> SEQUENCE: 64
cctcctctcc ctcccagagt ctgatgcaat t   31

<210> SEQ ID NO 65
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 29 non-resistance allele

<400> SEQUENCE: 65
attcattaat ccagctatag ttactggcac c   31

<210> SEQ ID NO 66
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 30 non-resistance allele

<400> SEQUENCE: 66
tgccagagac ccccactgga gcgttcaggg t                              31

<210> SEQ ID NO 67
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 31 non-resistance allele

<400> SEQUENCE: 67
agtcaaccgc agtaccgaag caagactgta g                              31

<210> SEQ ID NO 68
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 32 non-resistance allele

<400> SEQUENCE: 68
cggaccagga gacagggacc catcatttca t                              31

<210> SEQ ID NO 69
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 33 non-resistance allele

<400> SEQUENCE: 69
gcaatgttca tcctgtttaa ttcaccaaat g                              31

<210> SEQ ID NO 70
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 34 non-resistance allele

<400> SEQUENCE: 70
cgctacagaa atgacagaaa atacacactt c                              31

<210> SEQ ID NO 71
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 35 non-resistance allele

<400> SEQUENCE: 71
agatttagga gggttcgctc aaaataagaa a                              31

<210> SEQ ID NO 72

```
<211> LENGTH: 31
<212> TYPE: DNA
<213> ORGANISM: Salmo salar
<220> FEATURE:
<221> NAME/KEY: allele
<222> LOCATION: (1)..(31)
<223> OTHER INFORMATION: Polymorphism 36 non-resistance allele

<400> SEQUENCE: 72
ttattcggtg gtacccactc tcagaaatct t                             31
```

METHODS FOR DETECTING DNA POLYMORPHISMS IN ATLANTIC SALMON

The present invention relates to methods for predicting resistance to infectious pancreatic necrosis in salmon, more specifically the invention relates to predicting such resistance by the analysis of DNA polymorphisms.

Infectious pancreatic necrosis (IPN) is one of the major threats to the salmon farming industry worldwide. The disease is caused by an aquatic birnavirus, causing necrosis of pancreatic cells and liver cells, resulting in lethargy and sudden mortality. The virus is wide-spread in nature, but does not seem to affect free-living salmon to any large extent. In aquaculture environments, the disease causes mortalities both at the fry stage, when the fish are still living in fresh water, and at the post-smolt stage, shortly after transfer to sea water. The industry-wide losses due to IPN have been estimated to be 8% during the fresh water phase and 5% during the sea phase.

The salmon industry is, generally speaking, divided into several strata corresponding to the different life stages of the fish: egg producers sell fertilised eggs to producers of smolt, who provide salt-water-ready fish (smolt) to grow-out-producers. For each strata it is advantageous to select eggs or fish that are above-average resistant to diseases. Salmon breeding companies run continuous fish selection programmes aimed at improving the aquaculture stocks with regards to disease resistance, and protocols have been developed for testing of fish's resistance to several specific diseases. These challenge tests have been used in order to select fish as broodstock that possess above-average resistance to the diseases in question. Conventional tests involve controlled challenge-testing of siblings of the breeding candidates. This methodology is, however, impeded by the fact that infected fish cannot be used as broodstock. One therefore has to resort to selecting random (un-tested) animals from the families of the tested fish that performed best in the challenge tests (so-called family selection).

There is therefore a need for alternative methodologies for assaying animals' resistance to infectious pancreatic necrosis; particularly methodologies that allow direct assaying of individual's resistance to infectious pancreatic necrosis, whilst retaining the possibility of using the tested animal as broodstock.

The inventor of the present invention has, following extensive experimentation, identified that one can predict resistance to infectious pancreatic necrosis in salmon by analysis of one or more DNA polymorphisms (thereby satisfying the aforementioned need).

Accordingly, in a first aspect of the present invention, there is provided a method of predicting resistance to infectious pancreatic necrosis in salmon, the method comprising determining the alleles present at a DNA polymorphism in the salmon and predicting whether or not the salmon is resistant to infectious pancreatic necrosis based on the determination of the alleles.

The inventor has found that the DNA polymorphisms of the present invention can be present in either of two forms, i.e. the polymorphisms have two alleles. One allele can be characterised as being predictive of resistance to infectious pancreatic necrosis (i.e. the resistance allele); the other being predictive of non-resistance to infectious pancreatic necrosis (i.e. non-resistance allele). Salmon are diploid organisms, and so possess two copies of the polymorphisms of the present invention (one copy to be found in each set of chromosomes). The step of determining the alleles in the method of the first aspect of the present invention therefore includes the step of analysing the DNA polymorphism provided in each set of chromosomes in order to determine whether each copy of the DNA polymorphism present is a resistance allele or is a non-resistance allele. When a salmon subjected to the method of the present invention is determined to have two copies of the resistance allele for the DNA polymorphism (i.e. the salmon is homozygous for the resistance allele), the salmon is predicted to have resistance to infectious pancreatic necrosis. Conversely, when a salmon subjected to the method of the present invention is determined to have two copies of the non-resistance allele for the DNA polymorphism (i.e. is homozygous for the non-resistance allele), the salmon is predicted not to have resistance to infectious pancreatic necrosis. It may be concluded that a salmon that is predicted by the method of the present invention as having infectious pancreatic necrosis resistance has a greater than normal chance of having infectious pancreatic necrosis resistance. Conversely, it may be concluded that a salmon that is predicted not to have infectious pancreatic necrosis resistance has a lower than normal risk of developing infectious pancreatic necrosis resistance. When a salmon subjected to the method of the present invention is determined to have one copy of the resistance allele for the DNA polymorphism and one copy of the non-resistance allele for the DNA polymorphism (i.e. is heterozygous), the salmon would not be predicted according to the present invention to have resistance to infectious pancreatic necrosis. However, that salmon would be predicted to have a greater chance of being resistant to infectious pancreatic necrosis than a salmon with two copies of the non-resistance allele. Henceforth, such as salmon will be referred to as having semi-resistance to infectious pancreatic necrosis.

The DNA polymorphism in question can be any of several DNA polymorphisms found by the inventor to have this predictive ability. All of these DNA polymorphisms are located on chromosome 26. The DNA polymorphisms are linked by their common feature of predicting resistance to IPN resistance. The ability of the DNA polymorphisms to predict resistance to IPN can be quantified using the $r^2$ statistic, which will be explained below. All the DNA polymorphisms share the characteristic that this $r^2$ statistic is larger than 0.3. The DNA polymorphism may be a multiple nucleotide polymorphisms (ie non-SNP polymorphisms) a single nucleotide polymorphism, an addition mutation, or a deletion mutation. Each type of DNA polymorphism provided above are contemplated individually as part of the present invention for the step of determining in the methods of the present invention.

The DNA polymorphism may be selected from any of the DNA polymorphisms provided in Table 1. Each of the DNA polymorphisms provided in Table 1 are contemplated individually as part of the present invention.

The DNA polymorphisms described throughout this application are defined with reference to the whole genome sequence for Salmo solar published in genebank under accession number AGKD00000000 (version AGKD00000000.1 GI: 354459050). More particularly, each DNA polymorphism in the present application derives its name as described herein from the following: Genbank accession number, followed by underscore ('_') followed by the position of the DNA polymorphism within the GenBank sequence, followed by square brackets enclosing the reference allele (appearing first) and the alternative allele (appearing second). The reference allele is the allele appearing in the reference sequence.

For example, the DNA polymorphism may be:

```
AGKD01281000.1_4157[T/TA];

AGKD01281000.1_5527[T/TAT];

AGKD01021775.1_19790[G/A];

AGKD01281000.1_5251[A/G],
or;

AGKD01281000.1_4338[A/T].
```

Each of the above DNA polymorphisms are contemplated individually as part of the present invention.

The method may employ two DNA polymorphisms. When the method is employed with two DNA polymorphisms, the two DNA polymorphisms constitute one unit, hereafter referred to as a haplotype. Each haplotype can have four different alleles, corresponding to the four different combinations of DNA polymorphism alleles at the individual DNA polymorphisms (for example, if the haplotype is made up of one DNA polymorphism with alleles A and T, and one DNA polymorphisms with alleles T and G, the four possible haplotype alleles are A-T, A-G, T-T, and T-G). Each of these four alleles would be either a resistance allele or a non-resistance allele, in a manner analogous to the single DNA polymorphism method laid out above. Thus, in the hypothetical case of a haplotype having the four alleles A-T, A-G, T-T, and T-G, it could be that all A-T, A-G, and T-T were resistance alleles, whereas T-G was a non-resistance allele. In that case, an animal having one copy of the A-T allele and one copy of the A-G allele would be resistant to IPN, an animal having one copy of A-T and one copy of T-G would be semi-resistant, while an animal having two copies of T-G would be non-resistant.

The inventor has discovered a large number of such haplotypes, i.e. combinations of two DNA polymorphisms, that are powerful predictors of resistance to IPN, more powerful than single DNA polymorphisms. For each of these haplotypes, the inventor has identified which alleles are resistance alleles and which alleles are non-resistance alleles. The pairs of DNA polymorphisms that make up predictive haplotypes are either any combination of DNA polymorphisms listed in Table 1, or they are any combinations of one DNA polymorphism from Table 1 with one DNA polymorphism from Table 2. All predictive haplotypes are listed in Table 3, where the DNA polymorphisms are denoted by numbers relative to Tables 1 and Table 2. Each of the pairs of DNA polymorphisms are contemplated for use individually as part of the present invention. All pairs of DNA polymorphisms share the characteristic that their $r^2$ value (to be described below) is larger than 0.6.

Consequently, the present invention may therefore relate to a method that further comprises the step of determination of the allele present at a further DNA polymorphism, and a prediction of whether or not the salmon is resistant to infectious pancreatic necrosis is based on the determination of the alleles at both DNA polymorphisms.

For example, the method of the present invention may include the determination of alleles present at the DNA polymorphism AGKD01458345.1_5634[G/T], and at the further DNA polymorphism AGKD01021775.1_19790[G/A], and a prediction of whether or not the salmon is resistant to infectious pancreatic necrosis is based on the determination of the alleles at both DNA polymorphisms.

When haplotypes of two DNA polymorphisms rather than single DNA polymorphisms are used for predicting resistance, the haplotype alleles must first be determined in the tested fish, in other words, it must be determined which alleles at the individual DNA polymorphism are located on the same chromosomes. This can be done using computer programs such as PHASE (website stephenslab.uchicago.edu/software.html#phase), although for most animals the haplotype alleles will be evident (e.g. if an animal has two copies of allele A at one DNA polymorphism, and one copy of T and one copy of G at the other DNA polymorphism, only two configurations of alleles at the haplotype is possible, namely A-G+A-T).

When a haplotype of two DNA polymorphisms are used rather than one DNA polymorphism, the test becomes more predictive compared to when only one DNA polymorphism is used.

The method may involve analysis of more than two DNA polymorphisms. For example, the method of the present invention may involve the determination of more than two polymorphisms, wherein at least one of the polymorphisms is provided in table 1 and/or at least two of the polymorphisms are provided as a pair in table 3.

The method may be applied to Atlantic salmon (i.e. Salmo solar).

The step of determining the presence or absence in a salmon may be practised on a sample taken from the salmon. The sample may be any sample in which analysis of nucleic acid material is possible, as would be readily understood by the person skilled in the art. For the avoidance of doubt, the sample may be a muscle tissue sample, blood sample, liver sample and/or a fin clip.

The skilled person would be well aware of all available methods capable of testing for the presence or absence of a DNA polymorphism. For example, the method may involve sequence analysis of the salmon to be tested. Alternatively, the method may involve single base extension of DNA fragments terminating at the polymorphic site (e.g. iPLEX assays from Sequenom and Infinium assays from Illumina), allele-specific PCR (e.g. SNPtype assays from Fluidigm or KASPar assays from KBiosciences), or competitive hybridisation of probes complementary to the different alleles (e.g. the TaqMan assay from Applied Biosystems).

Consequently, in a further aspect of the present invention, there is provided a hybridisation probe that is specific for one or more of the aforementioned DNA polymorphisms.

The DNA at and around the DNA polymorphisms can be extrapolated from the names given to the DNA polymorphisms in Table 1 and Table 2. In addition, the DNA sequences at and around the DNA polymorphisms can be found in Table 4. Hybridisation probes that are selective for these DNA sequences may form part of the present invention.

A salmon that is predicted to have resistance to infectious pancreatic necrosis according to the first aspect of the present invention is more likely than normal to produce offspring that have a higher than normal chance of having resistance to infectious pancreatic necrosis. Consequently, in a further aspect of the present inventions, there is provided a method of selecting a salmon for use as broodstock, wherein the salmon is selected, based on the prediction by the method as claimed in the first aspect of the present invention, to have resistance to infectious pancreatic necrosis.

Conversely, a salmon predicted by the method of the first aspect of the present invention as not having resistance to infectious pancreatic necrosis would not be selected as broodstock.

The present invention also relates to an isolated polynucleotide comprising one or more of the single DNA polymorphisms selected from the group provided in Table 1 located within a portion of the salmon genome. Exemplary sequences for such isolated polynucleotides may be found in Table 4.

The terms "haplotype allele" and "DNA polymorphism allele" take their normal meaning as would be well understood by the person skilled in the art. However, for the avoidance of doubt "DNA polymorphism allele" may mean one of two different nucleotide sequences at the site of a DNA polymorphism of the present invention (one allele being the "resistance allele", the other being the "non-resistance allele"). However, for the avoidance of doubt, "haplotype allele" may mean one of four possible pairs of DNA polymorphism alleles of the present invention.
or:
. . . "haplotype allele" may mean any possible unique combination of alleles for that haplotype, i.e. any unique combination of one allele from each of the DNA polymorphisms constituting the haplotype (in the context of haplotypes constituted by two bi-allelic DNA polymorphisms, four such combinations are possible)

BRIEF DESCRIPTION OF THE DRAWINGS

The present invention will now be described by way of example with reference to the accompanying figures, in which.

1. SELECTION OF TEST ANIMALS

Figure 1:
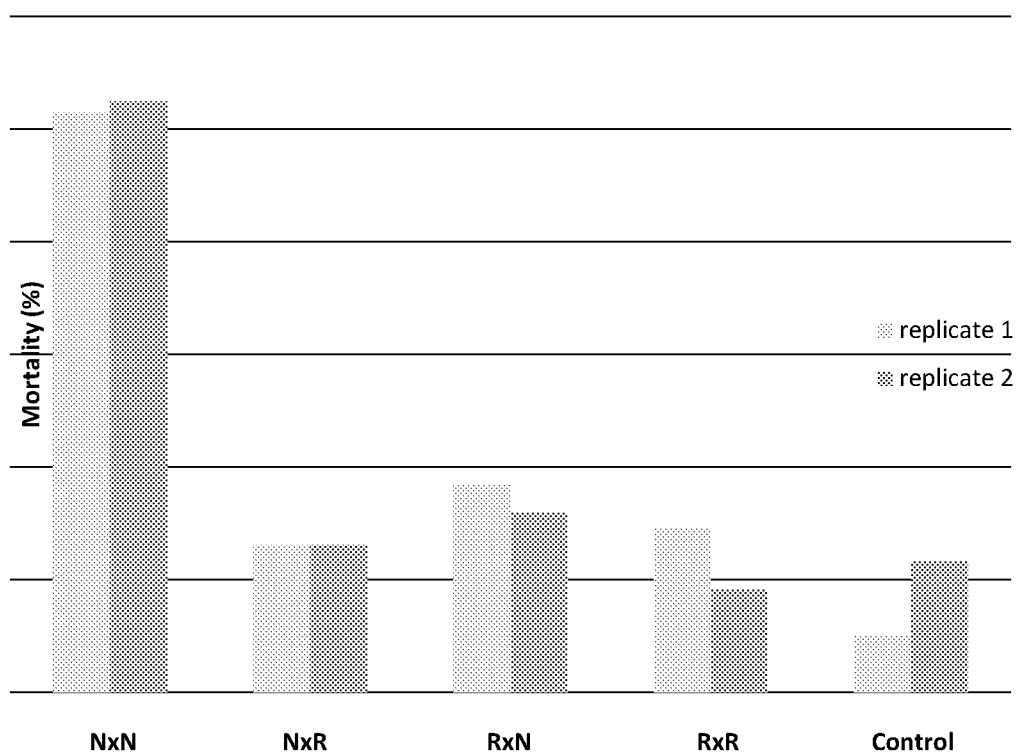
FIG. 1 shows a graph illustrating survival rates of salmon in an infectious pancreatic necrosis-challenge test.

Forty-five Atlantic salmon from the Aqua Gen breeding nucleus in Norway (selected from among the parents of the 2005 and 2008 year classes) were chosen for massive parallel sequencing (Illumina Hi Seq 2000). All salmon in the breading nucleus are derived from salmon taken from Norwegian rivers.

A Quantitative Trait Loci (QTL) has been linked with IPN resistance in Atlantic Salmon (Moen et al. 2009). Three single DNA polymorphisms were recently reported as being associated with the QTL (Houston et al. 2012), but a test for deducing whether individual animals are resistant or non-resistant has not been presented. The QTL is located on chromosome 26.

We assume here that the above-mentioned QTL for resistance to IPN is caused by an underlying but unknown mutation within a gene or other functional DNA element. This unknown mutation will hereafter be referred to as the quantitative trait nucleotide (QTN). It is further assumed that the QTN has two alleles; one allele that gives increased resistance (resistance allele, Q) and one allele that gives decreased resistance (non-resistance allele, q).

Four hundred and fifty-four full-sib groups of Atlantic salmon fry were challenged in individual tanks shortly after the start of feeding (protocols for a standard challenge test can be found in Moen et al. 2009. Each full-sib group consisted of 103 fish (on average), and tissue samples were collected from the 10 first-to-die within group as well as 10 survivors (or 10 last-to-die), whereupon DNA was extracted using the DNAeasy kit from QIAGEN (QIAGEN, Venlo, the Netherlands). From 206 selected full-sib groups, affected and surviving offspring were genotyped with three microsatellite markers located within the region of the QTL for IPN resistance; Alu333, Ssa0384BSFU/ii and Ssa0285BSFU, whereupon the linkage phase between alleles of the three microsatellites were identified in each mapping parent using the observed co-segregation of alleles from parents to offspring (genotyping of microsatellite markers are discussed in more detail in Moen et al. 2009). This genotyping was done in an iterative fashion so that, ultimately, almost all full-sib groups that were likely to have at least one QTN-heterozygous parent (see below) were genotyped. A chi-square test was applied in order to test for co-inheritance of the three-microsatellite haplotype and the affected/resistant phenotype, thereby identifying 110 QTN-heterozygous parents. Using data from these QTN-heterozygous parents, a table was created linking alleles at the three-microsatellite haplotype to QTN alleles. (If a three-microsatellite allele was found to be linked to both Q and q, only the most prevalent linkage phase was entered into the table.) This table was next used to extrapolate genotypes at the QTN for the mapping parents found to be QTN homozygous, as well as for other animals from the Aqua Gen breeding nucleus. Twenty-two Aqua Gen animals deduced in this way to have the QTN genotype QQ (i.e. expected to provide good IPN resistance), as well as 23 Aqua Gen animals likewise found to have the qq genotype (i.e. expected to provide poor IPN resistance), were chosen for subsequent whole-genome sequencing. These sets of 22 and 23 animals were put together in such a way as to minimise the relatedness of animals within the group, by maximising the diversity of three-microsatellite alleles within each group.

2. MAKING A REFERENCE DNA SEQUENCE ASSEMBLY FOR THE QTL REGION

QTL region was defined as the region in between the SNPs ESTNV_31602_808 and GCR_cBin30387_Ctg1_91 on the Atlantic salmon SNP linkage map (Lien et al. 2011). Bacterial Artificial Chromosome (BAC) clones matching these SNPs were isolated from an existing BAC library (Thorsen et al. 2004). On the basis of a physical map made from this library (www.asalbase.org), a minimum tiling path of 31 BACs was made (Table 5). Atlantic salmon genomic (i.e. insert) DNA was extracted from each BAC. An individually tagged paired-end library (with average insert size 350 bp) was made for each BAC DNA sample, whereupon the samples were sequenced in multiplex on a HiSeq2000 (Illumina Inc., San Diego, USA) to an average depth of approximately 800 times haploid genome coverage. Following removal of residual adapter sequences, discarding of too-short reads, trimming of the ends of poor quality reads, and matching of paired-end reads, a de novo assembly was made within each BAC using the Tcic_novo_assemble program from the CLC Assemble Cell suite (CLC Bio, Aarhus, Denmark). Phrap version 1.090518 (http://phrap.org.) was then used to assemble individual BAC contig sequences into a set of contigs spanning all BACs. Finally, the contigs from this reference were combined into one contiguous genomic scaffold by aligning it with scaffolds from a preliminary version of the Atlantic salmon genome sequence (which had been made in-house, using the Celera Assembler software, based on the data from the first 27 batches of sequences submitted by the sequencing project into the NCBI Trace Archive).

TABLE 5

Bacterial Artificial Chromosome (BAC) constituting a minimum tiling path found to span the QTL region.

| S0042J22 | S0004K18 | S0161O04 | S0243D12 |
| S0076E15 | S0021H01 | S0162F10 | S0258L08 |
| S0119L01 | S0026N22 | S0162J03 | S0259M06 |
| S0120O19 | S0048P16 | S0170B06 | S0262M03 |
| S0126K07 | S0063G22 | S0201A04 | S0282P22 |
| S0457C13 | S0066E05 | S0215J07 | S0344A15 |
| S0001F22 | S0115B04 | S0227H08 | S0449E20 |
| S0001N03 | S0160J02 | S0236E20 | |

3. DISCOVERY OF DNA POLYMORPHISMS PREDICTIVE OF IPN

The above-mentioned 23 QQ animals and 22 qq-animals were sequenced using HiSeq2000 technology from Illumina. Individually tagged paired-end libraries were made from each sample, before samples were pooled for sequencing. A total of $264 \times 10^9$ reads was produced, corresponding to a per-animal coverage of two times the haploid genome. The reads were assembled onto the above-mentioned QTL-region reference sequence using the programs 'clc_ref_assemble_long' and 'clc_ref_assemble' from the CLC Assembly Cell suite, producing two assemblies corresponding to the two QTN genotype groups. A matching length fraction of 0.9 and a minimum similarity of 0.98 was stipulated in an attempt to minimise the mapping of reads from homologous chromosomes. SNP detection was performed on these separate assemblies using the program 'find_variations' from the CLC Assembly Cell suite, allowing a minimum of one nucleotide difference to the reference base. A Fisher's exact test was used in order to test for independence between QTN genotype (i.e. assembly) and SNP/indel alleles. The SNPs with the most significant statistics from this exact were genotyped in the 110 QTN-heterozygous animals mentioned above, as well as in the challenge-tested offspring of those animals, and a Fisher's exact test was performed in order to test for independent inheritance of SNP alleles and QTN alleles. The correlation coefficient ($r^2$) between alleles at the SNP and at the QTN, a measure of the degree of linkage disequilibirum (LD) between loci, was also calculated for each SNP, using the 'LD' function of the 'genetics' module of the R statistical program suite. A SNP was defined as useful for predicting resistance to IPN if it had an $r^2$ value above 0.3 (this is a common assumption among geneticists, see e.g. Shifman et al., Human Molecular Genetics 2003). In the present context, the $r^2$ value is the fraction of allelic variation of the QTL explained by the predictive DNA polymorphism. For example, if $r^2=0.5$, twice as many animals must be genotyped for the predictive DNA polymorphism relative to a hypothetical case where the predictive DNA polymorphisms is the QTN itself.

SNPs identified as most strongly correlating with IPN resistance are provided in Table 1.

TABLE 1

DNA polymorphisms strongly associated with resistance to IPN.

| DNA polymorphism # | DNA polymorphism name | resistance allele/non-resistance allele | $r^2$ |
|---|---|---|---|
| 1 | AGKD01281000.1_4157[T/TA] | T/TA | 0.57 |
| 2 | AGKD01281000.1_5527[T/TAT] | T/TAT | 0.57 |
| 3 | AGKD01021775.1_19790[G/A] | G/A | 0.57 |
| 4 | AGKD01281000.1_5251[A/G] | A/G | 0.54 |
| 5 | AGKD01281000.1_4338[A/T] | A/T | 0.54 |
| 6 | AGKD01317469.1_245[T/A] | T/A | 0.54 |
| 7 | AGKD01281000.1_5457[A/G] | A/G | 0.54 |
| 8 | AGKD01028155.1_12812[A/G] | A/G | 0.5 |
| 9 | AGKD01452978.1_5956[A/G] | A/G | 0.41 |
| 10 | AGKD01039267.1_12921[T/A] | T/A | 0.41 |
| 11 | AGKD01059002.1_4664[T/C] | T/C | 0.4 |
| 12 | AGKD01451885.1_830[T/G] | T/G | 0.4 |
| 13 | AGKD01003456.1_35321[A/G] | A/G | 0.37 |
| 14 | AGKD01059002.1_16264[G/A] | G/A | 0.36 |
| 15 | AGKD01452978.1_6935[A/G] | A/G | 0.35 |
| 16 | AGKD01003456.1_36664[G/T] | G/T | 0.35 |
| 17 | AGKD01340746.1_282[C/T] | C/T | 0.35 |
| 18 | AGKD01062103.1_13615[T/G] | T/G | 0.32 |

TABLE 1-continued

DNA polymorphisms strongly associated with resistance to IPN.

| DNA polymorphism # | DNA polymorphism name | resistance allele/non-resistance allele | $r^2$ |
|---|---|---|---|
| 19 | AGKD01062103.1_13695[T/C] | T/C | 0.32 |
| 20 | AGKD01007787.1_13666[G/A] | G/A | 0.31 |
| 21 | AGKD01059002.1_3603[T/G] | T/G | 0.31 |

$r^2$ = the fraction of allelic variation at the QTN explained by the DNA polymorphism.

4. DISCOVERY OF TWO-DNA-POLYMORPHISM HAPLOTYPES PREDICTIVE OF RESISTANCE TO IPN

The genotypes of DNA polymorphisms on QTN-heterozygous parents and their challenge-tested offspring, described above, was also used in order to find combinations of 2 DNA polymorphisms that were more predictive of IPN resistance than the most predictive single DNA polymorphisms. The DNA polymorphisms were combined in all possible two-way combinations, and for each haplotype consisting of two DNA polymorphisms, haplotype alleles were identified for each QTN-heterozygous parent, and a Fisher exact test was used in order to test for independence between haplotype allele and QTN alleles. The correlation coefficient ($r^2$) between allelic states at the two-SNP haplotype and at the QTN was calculated by first mapping the two-SNP haplotype down to a two-allele system by replacing each allele name with the name of the QTN allele that the two-SNP haplotype allele in question was predominantly linked to (see Table 3), followed by calculation of $r^2$ using the 'LD' function of the 'genetics' module of the R statistical program suite.

The haplotypes predictive of resistance to IPN, identified in this manner, were either combinations of two DNA polymorphisms from Table 1, or they were combinations of one DNA polymorphism from Table 1 and one DNA polymorphism from Table 2. Table 3 contains all the combinations of DNA polymorphisms found to have an $r^2$ value larger than 0.60. Table 3 also contains the identity of the haplotypes alleles found for the respective predictive haplotypes, as well as the classification (resistant vs. non-resistant) of these haplotypes alleles.

Table 4 contains the DNA sequences of the DNA polymorphisms. These sequences can also be deduced on the basis of the DNA polymorphism names, as noted above.

TABLE 2

Auxiliary DNA polymorphisms, forming diagnostic pairs of DNA polymorphisms in combination with DNA polymorphisms from Table 1.

| DNA polymorphism # | DNA polymorphism name | resistance allele/non-resistance allele |
|---|---|---|
| 22 | AGKD01000927.1_15806[C/G] | C/G |
| 23 | AGKD01458345.1_5634[G/T] | T/G |
| 24 | AGKD01083029.1_8368[A/C] | C/A |
| 25 | AGKD01062103.1_13615[T/G] | T/G |
| 26 | AGKD01062103.1_13695[T/C] | T/C |
| 27 | AGKD01032349.1_7232[A/C] | A/C |
| 28 | AGKD01032349.1_14078[A/G] | G/A |
| 29 | AGKD01051656.1_1495[T/A] | A/T |
| 30 | AGKD01083029.1_5084[G/C] | C/G |
| 31 | AGKD01455926.1_1814[G/A] | A/G |
| 32 | AGKD01003456.1_1873[G/C] | G/C |
| 33 | AGKD01037589.1_572[C/T] | C/T |
| 34 | AGKD01037589.1_1369[C/A] | C/A |
| 35 | AGKD01205804.1_11559[A/G] | A/G |
| 36 | AGKD01106761.1_1717[T/C] | T/C |

TABLE 3

| DNA polymorphism #1 | DNA polymorphism #2 | r² | haplotype alleles |
|---|---|---|---|
| 1 | 23 | 0.84 | T-T(R), T-G(R), TA-T(R), TA-G(N) |
| 1 | 28 | 0.84 | T-G(R), T-A(R), TA-G(R), TA-A(N) |
| 2 | 23 | 0.84 | T-T(R), T-G(R), TAT-T(R), TAT-G(N) |
| 2 | 28 | 0.84 | T-G(R), T-A(R), TAT-G(R), TAT-A(N) |
| 3 | 23 | 0.84 | G-T(R), G-G(R), A-T(R), A-G(N) |
| 3 | 28 | 0.84 | G-G(R), G-A(R), A-G(R), A-A(N) |
| 4 | 23 | 0.81 | A-T(R), A-G(R), G-T(R), G-G(N) |
| 4 | 28 | 0.81 | A-G(R), A-A(R), G-G(R), G-A(N) |
| 5 | 23 | 0.81 | A-T(R), A-G(R), T-T(R), T-G(N) |
| 5 | 28 | 0.81 | A-G(R), A-A(R), T-G(R), T-A(N) |
| 6 | 23 | 0.81 | T-T(R), T-G(R), A-T(R), A-G(N) |
| 6 | 28 | 0.81 | T-G(R), T-A(R), A-G(R), A-A(N) |
| 7 | 23 | 0.81 | A-T(R), A-G(R), G-T(R), G-G(N) |
| 7 | 28 | 0.81 | A-G(R), A-A(R), G-G(R), G-A(N) |
| 1 | 11 | 0.79 | T-T(R), T-C(R), TA-T(R), TA-C(N) |
| 1 | 12 | 0.79 | T-T(R), T-G(R), TA-T(R), TA-G(N) |
| 2 | 11 | 0.79 | T-T(R), T-C(R), TAT-T(R), TAT-C(N) |
| 2 | 12 | 0.79 | T-T(R), T-G(R), TAT-T(R), TAT-G(N) |
| 3 | 11 | 0.79 | G-T(R), G-C(R), A-T(R), A-C(N) |
| 3 | 12 | 0.79 | G-T(R), G-G(R), A-T(R), A-G(N) |
| 4 | 11 | 0.78 | A-T(R), A-C(R), G-T(R), G-C(N) |
| 4 | 12 | 0.78 | A-T(R), A-G(R), G-T(R), G-G(N) |
| 5 | 11 | 0.78 | A-T(R), A-C(R), T-T(R), T-C(N) |
| 5 | 12 | 0.78 | A-T(R), A-G(R), T-T(R), T-G(N) |
| 6 | 11 | 0.78 | T-T(R), T-C(R), A-T(R), A-C(N) |
| 6 | 12 | 0.78 | T-T(R), T-G(R), A-T(R), A-G(N) |
| 7 | 11 | 0.78 | A-T(R), A-C(R), G-T(R), G-C(N) |
| 7 | 12 | 0.78 | A-T(R), A-G(R), G-T(R), G-G(N) |
| 1 | 31 | 0.76 | T-A(R), T-G(R), TA-A(R), TA-G(N) |
| 2 | 31 | 0.76 | T-A(R), T-G(R), TAT-A(R), TAT-G(N) |
| 3 | 31 | 0.76 | G-A(R), G-G(R), A-A(R), A-G(N) |
| 1 | 10 | 0.75 | T-T(R), T-A(R), TA-T(R), TA-A(N) |
| 2 | 10 | 0.75 | T-T(R), T-A(R), TAT-T(R), TAT-A(N) |
| 3 | 10 | 0.75 | G-T(R), G-A(R), A-T(R), A-A(N) |
| 4 | 31 | 0.74 | A-A(R), A-G(R), G-A(R), G-G(N) |
| 5 | 31 | 0.74 | A-A(R), A-G(R), T-A(R), T-G(N) |
| 6 | 31 | 0.74 | T-A(R), T-G(R), A-A(R), A-G(N) |
| 7 | 31 | 0.73 | A-A(R), A-G(R), G-A(R), G-G(N) |

TABLE 3-continued

| DNA polymorphism #1 | DNA polymorphism #2 | r² | haplotype alleles |
|---|---|---|---|
| 8 | 14 | 0.73 | A-G(R), A-A(R), G-G(R), G-A(N) |
| 1 | 22 | 0.72 | T-C(R), T-G(R), TA-C(R), TA-G(N) |
| 2 | 22 | 0.72 | T-C(R), T-G(R), TAT-C(R), TAT-G(N) |
| 3 | 22 | 0.72 | G-C(R), G-G(R), A-C(R), A-G(N) |
| 4 | 10 | 0.72 | A-T(R), A-A(R), G-T(R), G-A(N) |
| 5 | 10 | 0.72 | A-T(R), A-A(R), T-T(R), T-A(N) |
| 6 | 10 | 0.72 | T-T(R), T-A(R), A-T(R), A-A(N) |
| 7 | 10 | 0.72 | A-T(R), A-A(R), G-T(R), G-A(N) |
| 11 | 32 | 0.7 | T-G(R), T-C(R), C-G(R), C-C(N) |
| 11 | 33 | 0.7 | T-C(R), T-T(R), C-C(R), C-T(N) |
| 11 | 35 | 0.7 | T-A(R), T-G(R), C-A(R), C-G(N) |
| 12 | 24 | 0.7 | T-C(R), T-A(R), G-C(R), G-A(N) |
| 12 | 30 | 0.7 | T-C(R), T-G(R), G-C(R), G-G(N) |
| 12 | 32 | 0.7 | T-G(R), T-C(R), G-G(R), G-C(N) |
| 12 | 33 | 0.7 | T-C(R), T-T(R), G-C(R), G-T(N) |
| 12 | 35 | 0.7 | T-A(R), T-G(R), G-A(R), G-G(N) |
| 1 | 21 | 0.69 | T-T(R), T-G(R), TA-T(R), TA-G(N) |
| 2 | 21 | 0.69 | T-T(R), T-G(R), TAT-T(R), TAT-G(N) |
| 3 | 21 | 0.69 | G-T(R), G-G(R), A-T(R), A-G(N) |
| 4 | 22 | 0.69 | A-C(R), A-G(R), G-C(R), G-G(N) |
| 5 | 22 | 0.69 | A-C(R), A-G(R), T-C(R), T-G(N) |
| 6 | 22 | 0.69 | T-C(R), T-G(R), A-C(R), A-G(N) |
| 7 | 22 | 0.69 | A-C(R), A-G(R), G-C(R), G-G(N) |
| 1 | 18 | 0.68 | T-T(R), T-G(R), TA-T(R), TA-G(N) |
| 1 | 19 | 0.68 | T-T(R), T-C(R), TA-T(R), TA-C(N) |
| 1 | 25 | 0.68 | T-T(R), T-G(R), TA-T(R), TA-G(N) |
| 1 | 26 | 0.68 | T-T(R), T-C(R), TA-T(R), TA-C(N) |
| 1 | 27 | 0.68 | T-A(R), T-C(R), TA-A(R), TA-C(N) |
| 2 | 18 | 0.68 | T-T(R), T-G(R), TAT-T(R), TAT-G(N) |
| 2 | 19 | 0.68 | T-T(R), T-C(R), TAT-T(R), TAT-C(N) |
| 2 | 25 | 0.68 | T-T(R), T-G(R), TAT-T(R), TAT-G(N) |
| 2 | 26 | 0.68 | T-T(R), T-C(R), TAT-T(R), TAT-C(N) |
| 2 | 27 | 0.68 | T-A(R), T-C(R), TAT-A(R), TAT-C(N) |
| 3 | 18 | 0.68 | G-T(R), G-G(R), A-T(R), A-G(N) |
| 3 | 19 | 0.68 | G-T(R), G-C(R), A-T(R), A-C(N) |
| 3 | 25 | 0.68 | G-T(R), G-G(R), A-T(R), A-G(N) |
| 3 | 26 | 0.68 | G-T(R), G-C(R), A-T(R), A-C(N) |
| 3 | 27 | 0.68 | G-A(R), G-C(R), A-A(R), A-C(N) |

TABLE 3-continued

| DNA polymorphism #1 | DNA polymorphism #2 | r² | haplotype alleles |
|---|---|---|---|
| 4 | 21 | 0.68 | A-T(R), A-G(R), G-T(R), G-G(N) |
| 5 | 21 | 0.68 | A-T(R), A-G(R), T-T(R), T-G(N) |
| 6 | 21 | 0.68 | T-T(R), T-G(R), A-T(R), A-G(N) |
| 7 | 21 | 0.68 | A-T(R), A-G(R), G-T(R), G-G(N) |
| 11 | 24 | 0.67 | T-C(R), T-A(R), C-C(R), C-A(N) |
| 11 | 30 | 0.67 | T-C(R), T-G(R), C-C(R), C-G(N) |
| 4 | 18 | 0.65 | A-T(R), A-G(R), G-T(R), G-G(N) |
| 4 | 19 | 0.65 | A-T(R), A-C(R), G-T(R), G-C(N) |
| 4 | 25 | 0.65 | A-T(R), A-G(R), G-T(R), G-G(N) |
| 4 | 26 | 0.65 | A-T(R), A-C(R), G-T(R), G-C(N) |
| 4 | 27 | 0.65 | A-A(R), A-C(R), G-A(R), G-C(N) |
| 5 | 18 | 0.65 | A-T(R), A-G(R), T-T(R), T-G(N) |
| 5 | 19 | 0.65 | A-T(R), A-C(R), T-T(R), T-C(N) |
| 5 | 25 | 0.65 | A-T(R), A-G(R), T-T(R), T-G(N) |
| 5 | 26 | 0.65 | A-T(R), A-C(R), T-T(R), T-C(N) |
| 5 | 27 | 0.65 | A-A(R), A-C(R), T-A(R), T-C(N) |
| 6 | 18 | 0.65 | T-T(R), T-G(R), A-T(R), A-G(N) |
| 6 | 19 | 0.65 | T-T(R), T-C(R), A-T(R), A-C(N) |
| 6 | 25 | 0.65 | T-T(R), T-G(R), A-T(R), A-G(N) |
| 6 | 26 | 0.65 | T-T(R), T-C(R), A-T(R), A-C(N) |
| 6 | 27 | 0.65 | T-A(R), T-C(R), A-A(R), A-C(N) |
| 7 | 18 | 0.65 | A-T(R), A-G(R), G-T(R), G-G(N) |
| 7 | 19 | 0.65 | A-T(R), A-C(R), G-T(R), G-C(N) |
| 7 | 25 | 0.65 | A-T(R), A-G(R), G-T(R), G-G(N) |
| 7 | 26 | 0.65 | A-T(R), A-C(R), G-T(R), G-C(N) |
| 7 | 27 | 0.65 | A-A(R), A-C(R), G-A(R), G-C(N) |
| 1 | 29 | 0.63 | T-A(R), T-T(R), TA-A(R), TA-T(N) |
| 2 | 29 | 0.63 | T-A(R), T-T(R), TAT-A(R), TAT-T(N) |
| 3 | 29 | 0.63 | G-A(R), G-T(R), A-A(R), A-T(N) |
| 10 | 36 | 0.62 | T-T(R), T-C(R), A-T(R), A-C(N) |
| 11 | 34 | 0.62 | T-C(R), T-A(R), C-C(R), C-A(N) |
| 12 | 34 | 0.62 | T-C(R), T-A(R), G-C(R), G-A(N) |
| 14 | 20 | 0.62 | G-G(R), G-A(R), A-G(R), A-A(N) |
| 1 | 8 | 0.61 | T-A(R), T-G(R), TA-A(R), TA-G(N) |
| 2 | 8 | 0.61 | T-A(R), T-G(R), TAT-A(R), TAT-G(N) |
| 3 | 8 | 0.61 | G-A(R), G-G(R), A-A(R), A-G(N) |
| 4 | 29 | 0.61 | A-A(R), A-T(R), G-A(R), G-T(N) |
| 5 | 29 | 0.61 | A-A(R), A-T(R), T-A(R), T-T(N) |

TABLE 3-continued

| DNA polymorphism #1 | DNA polymorphism #2 | $r^2$ | haplotype alleles |
|---|---|---|---|
| 6 | 29 | 0.61 | T-A(R), T-T(R), A-A(R), A-T(N) |
| 7 | 29 | 0.61 | A-A(R), A-T(R), G-A(R), G-T(N) |
| 21 | 32 | 0.6 | T-G(R), T-C(R), G-G(R), G-C(N) |
| 21 | 33 | 0.6 | T-C(R), T-T(R), G-C(R), G-T(N) |
| 21 | 35 | 0.6 | T-A(R), T-G(R), G-A(R), G-G(N) |

Predictive combinations of two DNA polymorphisms (haplotypes). $r^2$=the fraction of allelic variation at the QTN explained by the haplotype; haplotype alleles=the valid alleles of the haplotype, T-G(R)=a haplotype having allele T at the DNA polymorphism #1, G at DNA polymorphism #2, being a resistance allele, TA-G(N)=a haplotype having allele TA at the DNA polymorphism #1, G at DNA polymorphism #2, being a non-resistance allele, etc. The numbering of the DNA polymorphisms is relative to Tables 1 and 2.

TABLE 4

| DNA polymorphism # | DNA polymorphism name | DNA sequence |
|---|---|---|
| 1 | AGKD01281000.1_4157[T/TA] | AAGTTCTTTTTTTTT[-/A]TATATGACTATCCTT [Seq. ID No.: 1/Seq. ID No.: 37] |
| 2 | AGKD01281000.1_5527[T/TAT] | TTGAGCACGTGTTTT[-/AT]GACGGTGTAGGAAGT [Seq. ID No.: 2/Seq. ID No.: 38] |
| 3 | AGKD01021775.1_19790[G/A] | ACGTACGCAGGCGCA[C/T]CCCTGCGATTTAGTG [Seq. ID No.: 3/Seq. ID No.: 39] |
| 4 | AGKD01281000.1_5251[A/G] | GGGAGGTCAGTGGGG[C/T]AGACAACTTAAAGCA [Seq. ID No.: 40/Seq. ID No.: 4] |
| 5 | AGKD01281000.1_4338[A/T] | TCTTCAGGAAAAAAA[A/T]ATATAATTAGTGATT [Seq. ID No.: 5/Seq. ID No.: 41] |
| 6 | AGKD01317469.1_245[T/A] | CTACAAACTTTCTCA[A/T]GGTATAGCAAAAAAT [Seq. ID No.: 42/Seq. ID No.: 6] |
| 7 | AGKD01281000.1_5457[A/G] | GAATGAAAGCACTTT[C/T]TTGGTATCCTATGCT [Seq. ID No.: 43/Seq. ID No.: 7] |
| 8 | AGKD01028155.1_12812[A/G] | GTCCTAACATTGAGC[C/T]GTGTTTGTTTGGCAG [Seq. ID No.: 44/Seq. ID No.: 8] |
| 9 | AGKD01452978.1_5956[A/G] | ACTATTTTATCTGGC[C/T]CTTTCAATCAGTCCT [Seq. ID No.: 45/Seq. ID No.: 9] |
| 10 | AGKD01039267.1_12921[T/A] | GATGATGGCCCCTAG[A/T]GAGTTACTGTAATGA [Seq. ID No.: 10/Seq. ID No.: 46] |
| 11 | AGKD01059002.1_4664[T/C] | ACATTATAAAAACAG[C/T]ATGAAGTGTACGTGT [Seq. ID No.: 47/Seq. ID No.: 11] |
| 12 | AGKD01451885.1_830[T/G] | CAGACAGACACCTAC[A/C]AGTAGGCTATGTGTT [Seq. ID No.: 12/Seq. ID No.: 48] |
| 13 | AGKD01003456.1_35321[A/G] | ACAAAGTAAGGTGGG[C/T]GGTGCAGAGTTAGGC [Seq. ID No.: 49/Seq. ID No.: 13] |
| 14 | AGKD01059002.1_16264[G/A] | AGTTTCAAATGAAAT[A/G]TGAATCCTTCAGGAT [Seq. ID No.: 50/Seq. ID No.: 14] |
| 15 | AGKD01452978.1_6935[A/G] | GGTGAAATCATCGTG[C/T]ATAGGCTATCACAGT [Seq. ID No.: 51/Seq. ID No.: 15] |
| 16 | AGKD01003456.1_36664[G/T] | GAGTACAGTGCACTC[A/C]GACAGACAGGCACAC [Seq. ID No.: 52/Seq. ID No.: 16] |
| 17 | AGKD01340746.1_282[C/T] | TTTTTGAGGAGGAGG[A/G]AAATACATTGTGTTC [Seq. ID No.: 53/Seq. ID No.: 17] |

TABLE 4-continued

| DNA polymorphism # | DNA polymorphism name | DNA sequence |
|---|---|---|
| 18 | AGKD01062103.1_13615[T/G] | TCTTTCACACATGAC[G/T]CCGTAATCCCGTTAC [Seq. ID No.: 54/Seq. ID No.: 18] |
| 19 | AGKD01062103.1_13695[T/C] | GCAGGCAGCGCTTGA[C/T]GGCGAATTGTTTTGA [Seq. ID No.: 55/Seq. ID No.: 19] |
| 20 | AGKD01007787.1_13666[G/A] | CATTTTATGCATTAT[A/G]TATCAGTGATGTTAC [Seq. ID No.: 56/Seq. ID No.: 20] |
| 21 | AGKD01059002.1_3603[T/G] | AGACATAGGCTCAAA[G/T]AATTCCTCACTGAGG [Seq. ID No.: 57/Seq. ID No.: 21] |
| 22 | AGKD01000927.1_15806[C/G] | AGTGTGTTGCACATC[C/G]TGTCATGCAGACAAT [Seq. ID No.: 22/Seq. ID No.: 58] |
| 23 | AGKD01458345.1_5634[G/T] | CACACTTTGTCAACA[A/C]ACACATATTATGTTA [Seq. ID No.: 23/Seq. ID No.: 59] |
| 24 | AGKD01083029.1_8368[A/C] | CTGCTAATGTCCTTT[G/T]GTGGGTTTCTTTTGG [Seq. ID No.: 24/Seq. ID No.: 60] |
| 25 | AGKD01062103.1_13615[T/G] | GTAACGGGATTACGG[A/C]GTCATGTGTGAAAGA [Seq. ID No.: 25/Seq. ID No.: 61] |
| 26 | AGKD01062103.1_13695[T/C] | TCAAAACAATTCGCC[A/G]TCAAGCGCTGCCTGC [Seq. ID No.: 26/Seq. ID No.: 62] |
| 27 | AGKD01032349.1_7232[A/C] | ACTCCCAGTGCTAAG[G/T]GAAGTCTCCAACATT [Seq. ID No.: 63/Seq. ID No.: 27] |
| 28 | AGKD01032349.1_14078[A/G] | CCTCCTCTCCCTCCC[A/G]GAGTCTGATGCAATT [Seq. ID No.: 64/Seq. ID No.: 28] |
| 29 | AGKD01051656.1_1495[T/A] | ATTCATTAATCCAGC[A/T]ATAGTTACTGGCACC [Seq. ID No.: 29/Seq. ID No.: 65] |
| 30 | AGKD01083029.1_5084[G/C] | TGCCAGAGACCCCCA[C/G]TGGAGCGTTCAGGGT [Seq. ID No.: 66/Seq. ID No.: 30] |
| 31 | AGKD01455926.1_1814[G/A] | AGTCAACCGCAGTAC[C/T]GAAGCAAGACTGTAG [Seq. ID No.: 67/Seq. ID No.: 31] |
| 32 | AGKD01003456.1_1873[G/C] | CGGACCAGGAGACAG[C/G]GACCCATCATTTCAT [Seq. ID No.: 32/Seq. ID No.: 68] |
| 33 | AGKD01037589.1_572[C/T] | GCAATGTTCATCCTG[C/T]TTAATTCACCAAATG [Seq. ID No.: 33/Seq. ID No.: 69] |
| 34 | AGKD01037589.1_1369[C/A] | CGCTACAGAAATGAC[A/C]GAAAATACACACTTC [Seq. ID No.: 70/Seq. ID No.: 34] |
| 35 | AGKD01205804.1_11559[A/G] | AGATTTAGGAGGGTT[C/T]GCTCAAAATAAGAAA [Seq. ID No.: 71/Seq. ID No.: 35] |
| 36 | AGKD01106761.1_1717[T/C] | TTATTCGGTGGTACC[C/T]ACTCTCAGAAATCTT [Seq. ID No.: 72/Seq. ID No.: 36] |

Sequences of the DNA polymorphisms listed in Table 1 and Table 2. The numbering is the same as the numbering in Table 1 and Table 2.

5. PROVING THE EFFECT OF THE SNP-ASSISTED SELECTION

Challenge 1: An experiment was set up in order to test the effect of implementing the SNP-haplotype-based DNA-test described above (1-4): Using the haplotype-based DNA test (with marker pair 3+23, see Table 3), 4 non-resistant males, 6 resistant males, 6 non-resistant females, and 4 resistant females were selected from the Aqua Gen breeding population. All males were crossed to all females, producing the four groups R×R, R×N, N×R, and N×N; R×R consisting of the offspring of resistant males and resistant females, R×N consisting of the offspring of resistant males and non-resistant females, N×R consisting of the offspring of non-resistant males and resistant females, and N×N consisting of the offspring of non-resistant males and non-resistant females. The groups were transported to the challenge test facilities (VESO Vikan, Namsos, Norway) at the average size of 0.2 g (pre-startfed fry), start-fed within 1 day of arrival, acclimatized according to Standard Operation Procedure (SOP) S-2023, tended and monitored on a daily basis according to S-2002 and S-2004. Dead fish were collected every day according to S-2000, and the mortalities were recorded. Environmental parameters were recorded daily. Each of the groups R×R, R×N, N×R, and N×N were tested in two tanks following a bath challenge model (S-1079).

Each tank had 100 fry from the corresponding group. Fresh (i.e. not frozen) infectious pancreatic necrosis virus was used, coming from an isolate of serotype SP 1, passage j.no. V-1244 (Norwegian field isolate from 2001), growth and titration of the virus being done at the Norwegian School of Veterinary Science (Oslo, Norway). Two additional tanks were included as controls, containing mock-challenged fish from all four groups. Results are provided in FIG. 1.

FIG. 1: Mortalities in an IPN challenge test performed on four different groups of fish produced using the method described in this application. According to the test, all fish in group N×N were non-resistant, all fish in groups N×R and R×N were semi-resistant, while all fish in group R×R were resistant. The fish in the control group were mock challenged, so that the mortalities in this group represent expected mortalities in the absence of virus.

Figure 2:
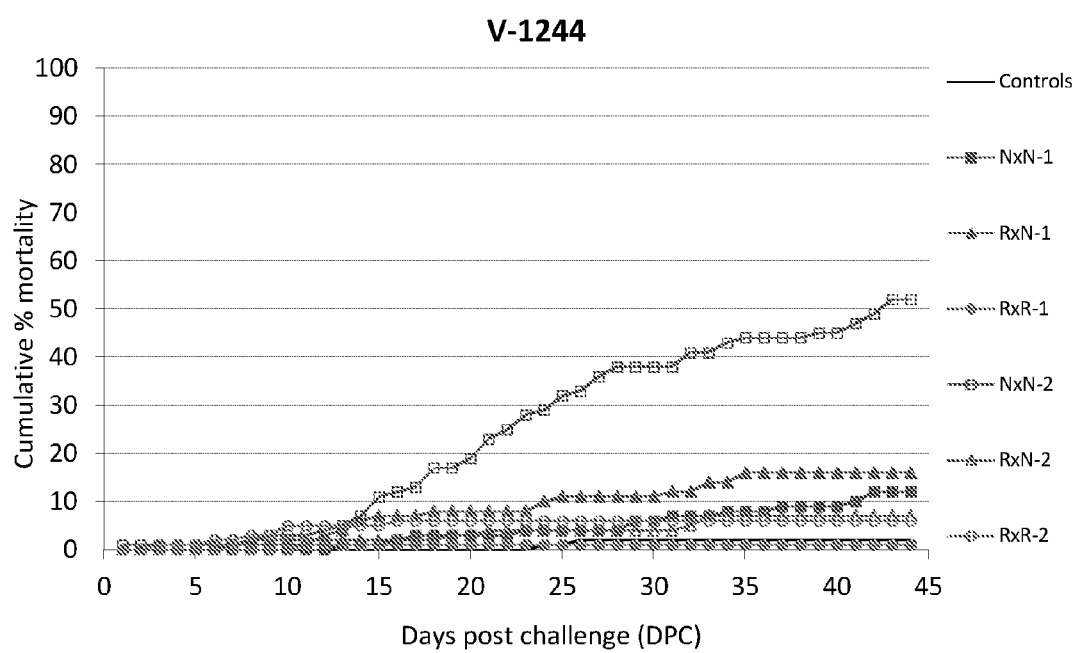
FIG. 2 shows a graph illustrating cumulative mortality in a bath challenge of salmon with standard virus isolate C-1244.

Challenge 2: This experiment was set up in order to compare the mortality due to the standard virus isolate V-1244 isolated in 2001 with the mortality due to a Norwegian field strain isolated in 2012 from a hatchery experiencing IPN-related mortality. Using the haplotype-based DNA test (with marker pair 3+23, see Table 3), 6 non-resistant males, 5 resistant males, 6 non-resistant females, and 6 resistant females were selected from the Aqua Gen breeding population. All males were crossed to all females, producing the four groups R×R, R×N, and N×N; R×R consisting of the offspring of resistant males and resistant females, R×N consisting of the offspring of resistant males and non resistant females as well as the offspring of non-resistant males and resistant females, and N×N consisting of the offspring of non-resistant males and non-resistant females. The groups were transported to the challenge test facilities (VESO Vikan, Namsos, Norway) at the average size of 0.2 g (pre-startfed fry), startfed within 1 day of arrival, acclimatized according to Standard Operation Procedure (SOP) S-2023, tended and monitored on a daily basis according to S-2002 and S-2004. Dead fish were collected every day according to S-2000, and the mortalities were recorded. Environmental parameters were recorded daily. Each of the groups R×R, R×N and N×N were tested in two parallel tanks for each virus strain (V-1244 and field strain) following a bath challenge model (S-1079). Each tank had 100 fry from the corresponding group. The V-1244 strain isolated in 2001 was prepared by the Norwegian School of Veterinary Science (Oslo, Norway), whereas the field strain was propagated and titrated by Vaxxinova Norway. Both virus isolates were kept refrigerated until challenge. One tank was included as a negative control, containing mock-challenged fish of all three genotypes. The challenge was terminated 45 days after challenge, and the results are provided in FIGS. 2 and 3. The results demonstrate that the R×R fish (as determined by the methods of the present invention) are fully resistant to both IPNV strains.

FIG. 2.

Figure 3:
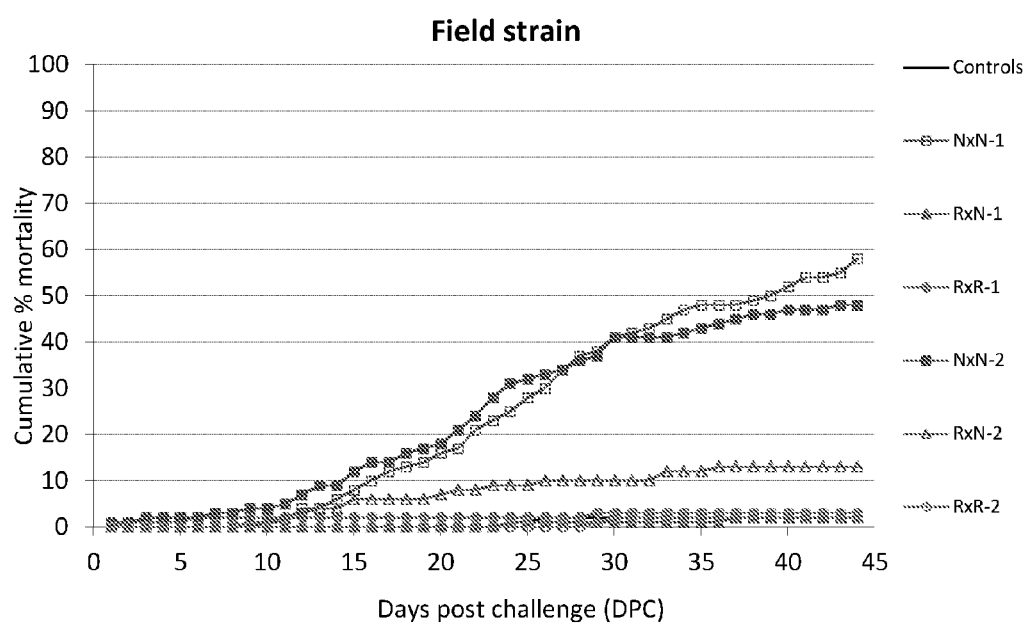
FIG. 3 shows a graph illustrating cumulative mortality in a bath challenge of salmon with a Norwegian field strain of IPN virus.

Cumulative mortality in a bath challenge of Atlantic salmon fry of differing IPN QTL genotypes challenged with a well known test isolate of IPNV, V-1244 (FIG. 2) or with a field strain isolateded from a hatchery in 2012 (FIG. 3).

6. COMPARISON OF KNOWN SNPS WITH THOSE OF THE PRESENT INVENTION

Houston et al. (2012 identified single nucleotide polymorphisms (SNPs) that were alleged to be associated with resistance to IPN. In their paper they reveal two SNPs (called Ssa0139ECIG and RAD_HT01) that are reported to have a particularly strong association to IPN-resistance. The SNP Ssa0139ECIG was first reported in a paper by Moen et al., but that study did not report any association to IPN-resistance. RAD_HT01 was reported for the first time by Houston et al. (2012).

The SNP RAD_HT01 was independently identified by the applicant as part of the sequencing-based screening for DNA polymorphisms associated with IPN resistance discussed above. However, the estimated association to IPN-resistance was found to be too weak to warrant further testing by genotyping; the p-value (the significance level of the SNP was 0.0199, whereas all the SNPs selected for testing by the present applicant genotyping had p-values below 0.005).

The SNP Ssa0139ECIG was not independently identified by the applicant, as this SNP was not covered by the reference DNA sequence used in the applicant's search for IPN-associated SNPs. Instead, the association between this SNP and IPN-resistance was tested by the applicant by genotyping the parents of IPN challenged fish, followed by statistical testing of the effect of SNP genotypes in these parents on mortality rates in their offspring (in the same manner discussed above for the present invention). The data set consisted of 285 full-sib groups with recorded mortality rates and genotyped parents. The SNP AGKD01021775.1_19790[G/A] provided in Table 1 was included in the analysis, as a positive control.

The association between the SNP and IPN resistance was tested using this linear model (one SNP at a time):

$$y=1\mu+(Z_s+Z_d)u+pb+e$$

where y is a vector of mortality rates for all full-sib groups, $\mu$ is the overall mean, u is a vector of random additive genetic effects of parents, $Z_s$ and $Z_d$ are sire and dam incidence matrices, p is a vector of SNP allele copies in the parents (0-4) for each full-sib group, b is the random regression coefficient associated with number of parental SNP alleles, and e is a vector of random residuals. Furthermore, u~N(0, A$\sigma_u^2$), b~N(0, $\sigma_b^2$), and e~N(0, I$\sigma_e^2$), where A is the numerator relationship matrix for the parents, $\sigma_u^2=\frac{1}{4}\sigma_g^2$, $\sigma_g^2$ is the total additive genetic (polygenic) variance, $\sigma_b^2$ is the variance of the random regression coefficient and $\sigma_e^2$ is the residual variance of full-sib group mortality rates.

Variance components were estimated for all random effects (additive genetic sire & dam, random regression of SNP effect and residual), using REML methodology with the DMU software (Madsen and Jensen 2008. To test the significance of a SNP, the full model was compared to a reduced model without the random regression on number of parental SNP alleles, using a likelihood ratio test.

The SNP Ssa0139ECIG was found to have no significant effect on the IPN mortality (p-value=0.64), whereas the SNP AGKD01021775.1_19790[G/A] were extremely significant (p-value=2.86E-18).

In the paper by Houston et al. (2012), the SNPs Ssa0139ECIG and RAD_HT01 are presented as having strong (and approximately equal) effects on IPN-resistance. The results described above indicate that the DNA polymorphisms described by Houston et al. (2012) have little or no effect on IPN resistance in the population tested, while the DNA polymorphisms described in the present application have strong and extremely significant effects.

REFERENCES

Houston R D, Haley C S, Hamilton A, Guy D R, Tinch A E, Taggart J B, McAndrew B J, Bishop S C (2008) Major quantitative trait loci affect resistance to infectious pancreatic necrosis in Atlantic salmon (Salmo salar). Genetics 178: 1109-15.
Houston R D, Davey J W, Bishop S C, Lowe, N R, Mota-Velasco J C et al. (2012) Characterisation of QTL-linked and genome-wide restriction site-associated DNA (RAD) markers in farmed Atlantic salmon. BMC Genomics 13: 244,
Lien S, Gidskehaug L, Moen T, Hayes B J, Berg P R, Davidson W S, Omholt S W, Kent M P (2011) A dense SNP-based linkage map for Atlantic salmon (*Salmo salar*) reveals extended chromosome homeologies and striking differences in sex-specific recombination patterns. BMC Genomics 12: 615.
Madsen and Jensen (2008) DMU: a user's guide. A package for analysing multivariate mixed models, version 6, release 5.0. University of Aarhus, Tjele, Denmark.
Moen T, Hayes B, Baranski M, Berg P R, Kjøglum S, Koop B F, Davidson W S, Omholt S W, Lien S (2008) A linkage map of the Atlantic salmon (Salmo salar) based on EST-derived SNP markers. BMC Genomics 9: 223.
Moen T, Baranski M, Sonesson A K, Kjøglum S (2009) Confirmation and fine-mapping of a major QTL for resistance to infectious pancreatic necrosis in Atlantic salmon (Salmo salar): population-level associations between markers and trait. BMC Genomics 10: 368.
Shifman S, Kuypers J, Kokoris M, Yakir B, Darvasi A (2003) Linkage diseuilibrium patterns of the human genome across populations. Human Molecular Genetics 12: 771-776.
Thorsen J, Zhu B, Frengen E, Osoegawa K, de Jong, P J, Koop B F, Davidson W S, Høyheim B (2005) A highly redundant BAC library of Atlantic salmon (Salmo salar): an important tool for salmon projects. BMC Genomics 6: 50.

REFERENCE TO A "SEQUENCE LISTING," A TABLE, OR A COMPUTER PROGRAM LISTING APPENDIX SUBMITTED AS AN ASCII TEXT FILE

The material in the ASCII text file, named "MURG-53865-Corrected-Sequence-Listing.txt", created Jul. 20, 2015, file size of 20,480 bytes, is hereby incorporated by reference.

The invention claimed is:

1. A method for detecting a DNA polymorphism in Atlantic salmon, the method comprising:
    obtaining a tissue sample from an Atlantic salmon;
    extracting DNA from said tissue sample;
    providing an allele-specific polynucleotide that hybridizes to either allele #1 or allele #2 of the DNA polymorphism, wherein the DNA polymorphism and allele #1 and allele #2 are:

| DNA Polymorphism No. | DNA polymorphism name | allele #1/ allele #2 |
|---|---|---|
| 2 | AGKD0128000.1_5527 | T/TAT | hybridizing the allele-specific polynucleotide to the extracted DNA; and detecting allele #1 or allele #2 of the DNA polymorphism based on the hybridization of the allele-specific polynucleotide to the extracted DNA.

2. The method of claim 1 wherein a fragment of DNA is used as said extracted DNA.

3. The method of claim 2 wherein the hybridizing step is employed in a process selected from polymerase chain reaction, probe hybridization, and competitive hybridization of probes.

4. A method of obtaining Atlantic salmon to be used as broodstock, the method comprising the steps of:
    carrying out the method as claimed in claim 1; and
    physically separating from a population of Atlantic salmon those Atlantic salmon in which allele #1 of the DNA polymorphism is detected, thereby obtaining Atlantic salmon to be used as broodstock.

5. The method of claim 1, wherein the method further comprises providing at least one additional allele-specific polynucleotide that hybridizes to either allele #1 or allele #2 of one of the following DNA polymorphisms; hybridizing the at least one additional allele-specific polynucleotide to the extracted DNA; and detecting hybridization of the at least one additional allele-specific polynucleotide to the extracted DNA as indicative of the presence of allele #1 or allele #2 of one of the following DNA polymorphisms:

| DNA Polymorphism No. | DNA polymorphism name | allele #1/ allele #2 |
|---|---|---|
| 1 | AGKD01281000.1_4157 | T/TA |
| 3 | AGKD01021775.1_19790 | G/A |
| 4 | AGKD01281000.1_5251 | A/G |
| 5 | AGKD01281000.1_4338 | A/T. |

6. The method of claim 1, wherein the method further comprises providing at least one additional allele-specific polynucleotide that hybridizes to either allele #1 or allele #2 of one of the following DNA polymorphisms; hybridizing the at least one additional allele-specific polynucleotide to the extracted DNA; and detecting hybridization of the at least one additional allele-specific polynucleotide to the extracted DNA as indicative of the presence of allele #1 or allele #2 of one of the following DNA polymorphisms:

| DNA Polymorphism No. | DNA polymorphism name | allele #1/ allele #2 |
|---|---|---|
| 1 | AGKD01281000.1_4157 | T/TA |
| 3 | AGKD01021775.1_19790 | G/A |
| 4 | AGKD01281000.1_5251 | A/G |
| 5 | AGKD01281000.1_4338 | A/T |
| 6 | AGKD01317469.1_245 | T/A |
| 7 | AGKD01281000.1_5457 | A/G |
| 8 | AGKD01028155.1_12812 | A/G |
| 9 | AGKD01452978.1_5956 | A/G |
| 10 | AGKD01039267.1_12921 | T/A |
| 11 | AGKD01059002.1_4664 | T/C |
| 12 | AGKD01451885.1_830 | T/G |
| 13 | AGKD01003456.1_35321 | A/G |
| 14 | AGKD01059002.1_16264 | G/A |
| 15 | AGKD01452978.1_6935 | A/G |
| 16 | AGKD01003456.1_36664 | G/T |
| 17 | AGKD01340746.1_282 | C/T |
| 18 | AGKD01062103.1_13615 | T/G |
| 19 | AGKD01062103.1_13695 | T/C |
| 20 | AGKD01007787.1_13666 | G/A |

-continued

| DNA Polymorphism No. | DNA polymorphism name | allele #1/ allele #2 |
|---|---|---|
| 21 | AGKD01059002.1_3603 | T/G |
| 22 | AGKD01000927.1_15806 | C/G |
| 23 | AGKD01458345.1_5634 | T/G |
| 24 | AGKD01083029.1_8368 | C/A |
| 25 | AGKD01062103.1_13615 | T/G |
| 26 | AGKD01062103.1_13695 | T/C |
| 27 | AGKD01032349.1_7232 | A/C |
| 28 | AGKD01032349.1_14078 | G/A |
| 29 | AGKD01051656.1_1495 | A/T |
| 30 | AGKD01083029.1_5084 | C/G |
| 31 | AGKD01455926.1_1814 | A/G |
| 32 | AGKD01003456.1_1873 | G/C |
| 33 | AGKD01037589.1_572 | C/T |
| 34 | AGKD01037589.1_1369 | C/A |
| 35 | AGKD01205804.1_11559 | A/G |
| 36 | AGKD01106761.1_1717 | T/C. |

\* \* \* \* \*

UNITED STATES PATENT AND TRADEMARK OFFICE
CERTIFICATE OF CORRECTION

PATENT NO. : 9,920,368 B2  
APPLICATION NO. : 14/412829  
DATED : March 20, 2018  
INVENTOR(S) : Thomas Moen Page 1 of 1

It is certified that error appears in the above-identified patent and that said Letters Patent is hereby corrected as shown below:

In the Claims

Column 49, Claim 1, Line 29 should read as follows:

| 2 | AGKD01281000.1_5527 | T/TAT |

Signed and Sealed this  
Fifth Day of June, 2018

Andrei Iancu  
*Director of the United States Patent and Trademark Office*